United States Patent [19]
Lee et al.

[11] Patent Number: 5,695,340
[45] Date of Patent: Dec. 9, 1997

[54] DENTAL RESTORATION SYSTEM AND METHOD

[75] Inventors: Henry L. Lee, Pasadena, Calif.; George Burbach, Chandlor, Ariz.

[73] Assignee: Lee Pharmaceuticals, South El Monte, Calif.

[21] Appl. No.: 494,518

[22] Filed: Jun. 26, 1995

[51] Int. Cl.$^6$ ............................................. A61C 5/00
[52] U.S. Cl. ............................... 433/226; 433/228.1
[58] Field of Search ................................ 433/215, 219, 433/226, 228.1, 229

[56] References Cited

U.S. PATENT DOCUMENTS

| | | | |
|---|---|---|---|
| 1,743,910 | 1/1930 | Boatner | 433/226 |
| 4,696,646 | 9/1987 | Maitland | 433/229 |
| 4,971,558 | 11/1990 | Jacobi | 433/226 |
| 4,993,951 | 2/1991 | Schumacher | 433/226 |
| 5,098,300 | 3/1992 | Zaki | 433/226 |
| 5,217,375 | 6/1993 | Oden et al. | 433/218 |
| 5,272,184 | 12/1993 | Shoher et al. | 433/226 |
| 5,358,406 | 10/1994 | Bjerknes | 433/226 |
| 5,368,831 | 11/1994 | Tanaka | 433/226 |
| 5,567,156 | 10/1996 | Hagne et al. | 433/226 |

*Primary Examiner*—Ren Yan
*Attorney, Agent, or Firm*—Walter A. Hackler

[57] ABSTRACT

A dental restoration system includes a plurality of proximal inlays of differing sizes for selection by a dentist to fit a prepared tooth cavity. In addition, a plurality of occlusal inlays is provided for covering the prepared tooth cavity and abutting the proximal inlays. In combination therewith, a curable restorative resin is provided for securing the proximal inlay in a blocking relationship with the end of a prepared tooth cavity and for securing the occlusal inlay to a bottom of the prepared tooth cavity and to the proximal inlay. The method of the present invention provides for forming a prepared tooth cavity and the utilization of curable restorative resins for providing modular-occlusal-distal (MOD) or modular-occlusal (MO) dental restorations using a modular preformed proximal and occlusal inlays to provide the usual appearance of an original natural tooth.

16 Claims, 5 Drawing Sheets

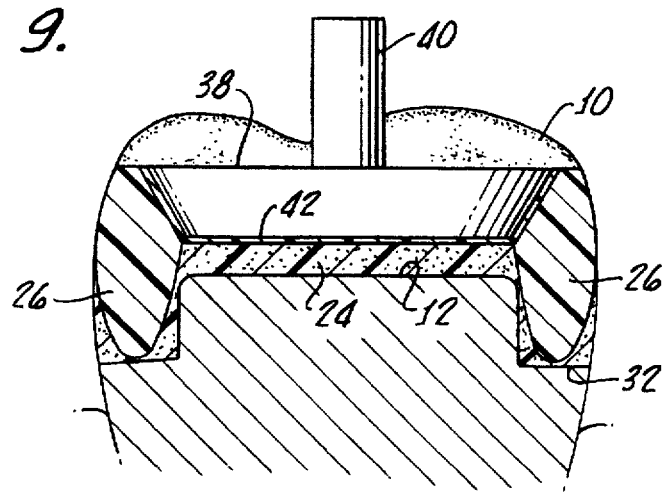
FIG. 9.
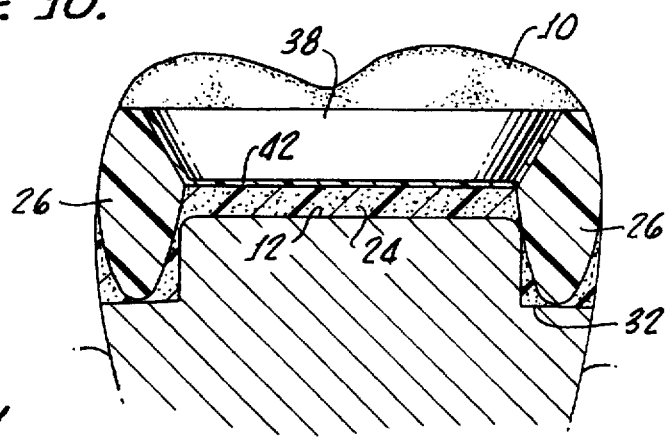
FIG. 10.
FIG. 11.
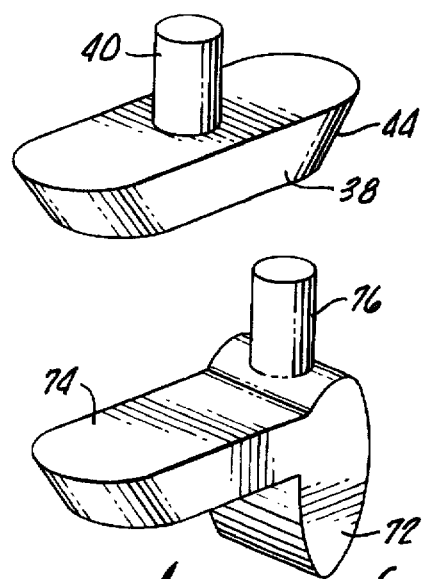
FIG. 12.
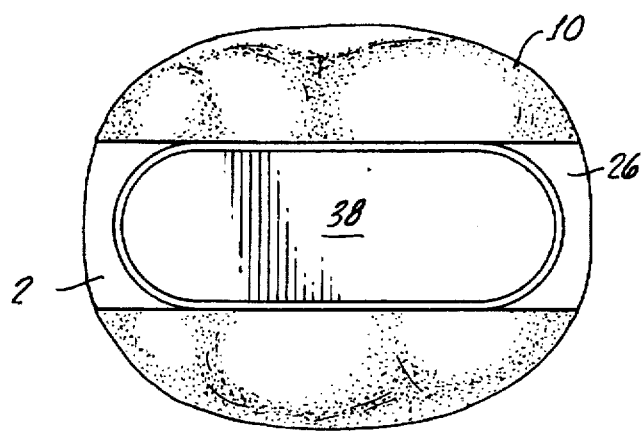
FIG. 17.

DENTAL RESTORATION SYSTEM AND METHOD

The present invention generally relates to dental restoration materials and methods and is more particularly directed to a system including modular preformed restorative complementary compatible components for the filling and restoring of posterior teeth.

Dental patients increasingly demand more aesthetically faithful restoration of decayed teeth. In addition, health concerns have arisen in connection with mercury amalgams. These problems have been addressed in several ways. Intraorally cured composites of various types have been proposed but found wanting. Polymerization shrinkage and difficulty in obtaining proximal contact and finishing the proximal areas are but a few of the problems reported with techniques for composites. Such restorations often exhibit inferior wear resistance and marginal strength.

Other approaches to the problem have been proposed. Direct or intraoral restorations are desirable because they provide the possibility for a conservative cavity outline. There is no need for removal of sound tooth structure in order to allow for a path of insertion and removal of a restoration. No impressions and lab work are required. Therefore, it is less expensive; there are fewer variables; and less time is required.

The disadvantages of direct restorations include greater difficulty in achieving good interproximal contact due to inability to condense the restorative material against the matrix band (as in the case of amalgam and gold foil restorations), weaker restorative material which will wear faster, and greater technique sensitivity.

The advantages of the indirect technique lie in the ability to minimize the disadvantages of the direct technique. The fillings can be fabricated of composites that are cured under heat and/or pressure, and/or light, of greater magnitude than those which can be used in the patient's mouth, and are therefore superior in strength, durability and friction resistance. On the other hand, the disadvantages lie in the need to have divergent walls which may require the unnecessary removal of sound tooth structure, the necessity of lab work and cementation of the final restoration and sometimes the necessity of temporization.

More recently, glass ceramic inserts have been proposed to provide a scaffold against which the polymerizable material is built up (Bowen, U.S. Pat. Nos. 4,521,550 and 4,744,759). It is reported that ceramic inserts decrease micro leakage, increase stiffness and durability of the composite and add dimensional stability to remaining tooth crown during hardening and function. One known system provides components for tooth restoration in the form of a preformed body which is used to create a contact with an adjacent tooth. The preformed body or insert is engaged with a handheld tool and is manually held in position during the filling/polymerization process (Maitland, U.S. Pat. No. 4,696,646 and Zaki, U.S. Pat. No. 5,098,300). This technique does not provide any universally applicable way of restoring teeth on both proximal and occlusal surfaces using a number of standardized preformed bodies.

The present invention relates to a system and method which enable the restoration of posterior teeth utilizing a maximum of durable synthetic material at occlusal and proximal surfaces. The method involves the use of a small number of modular proximal and occlusal inlays, said inlays generally fitting the cavity preparation otherwise and being bonded by adhesive bonding techniques or lutting agents based on restorative composite resins.

More particularly, this invention involves tight-fitting inlays much like an Inca stone wall. The dentist grinds into the inlays already bonded into place, so as to make a tight-fitting modular custom build-up of inserts. In general, so little restorative composite resin is needed that the restoration comes close to approaching a laboratory inlay made from impressions.

The method of this invention provides an improved dental restoration that has greater aesthetics than mercury silver amalgam or gold restorations. More significantly, the present invention provides superior restoration as compared to prior restorations based on quartz, porcelain or glass inlays and restorative resins. The individual modular inlays of this invention conjoin to provide a mosaic-like effect which approximates the original natural appearance of the tooth. At the same time, a highly wear-resistant surface is provided.

This invention is believed to represent a substantial advance in the art of dental restoration, and it is to be expected that this invention will be widely adopted by dental practitioners.

SUMMARY OF THE INVENTION

A dental restoration system in accordance with the present invention includes at least one proximal inlay which is sized for blocking an end of a prepared tooth cavity. Alternatively, a first proximal inlay and a second proximal inlay may be provided and sized for blocking at opposite ends of a prepared tooth cavity. Preferably, the dental restoration system, in accordance with the present invention, includes a plurality of proximal inlays with each of the proximal inlays being of different size for blocking ends of prepared tooth cavities. In this manner, a dentist has a spectrum of proximal inlays from which one may be chosen for an idividually prepared tooth cavity, with insertion being made in accordance with the method of the present invention, as hereinafter described.

Also, as part of the dental restoration system in accordance with the present invention, an occlusal inlay is provided of a size for covering the prepared tooth cavity and abutting the proximal inlay. Preferably, the dental restoration system in accordance with the present invention includes a plurality of occlusal inlays, each being of different size for providing the dentist with a spectrum of inlays for matching a prepared tooth cavity.

In addition, a curable restorative resin is provided for securing a proximal inlay in a blocking relationship with the end of the prepared tooth cavity and additionally securing the occlusal inlay to the bottom of the tooth cavity and to the proximal inlay.

More particularly, each of the proximal and occlusal inlays in accordance with the present invention is provided with handles for facilitating placement thereof in a restorative position with the prepared tooth cavity. As hereinafter set forth, in accordance with the method of the present invention, the handles are removed during final shaping of the restoration. The proximal and occlusal inlays may be composed of dental porcelain, or ceramic, or preferably composed of quartz, glass, or ceramic.

A method in accordance with the present invention utilizing the dental restoration system hereinabove set forth includes the steps of forming a prepared cavity, having at least one open end, in a tooth; thereafter partially filling the prepared tooth cavity with an uncured restorative resin.

A proximal inlay is positioned for blocking one end of the prepared cavity and into the uncured restorative resin. Following this placement, the restorative composite resin is cured by securing a proximal inlay therein. An occlusal cavity is then formed in the cured restorative composite resin and the secured proximal inlay which is followed by a partial filling of the occlusal cavity with additional uncured restorative resin.

A selected occlusal inlay has been disposed in the additional uncured restorative resin and against the secured proximal inlay. Following curing of the additional uncured restorative resin, excess additional restorative resin is removed and the secured occlusal and proximal inlays are shaped to an original tooth.

Additionally, the present invention includes a tooth restoration which is formed by the method hereinabove recited.

BRIEF DESCRIPTION OF THE DRAWINGS

The advantages and features of the present invention will be better understood by the following description when considered in conjunction with the accompanying drawings in which:

FIG. 9 is a cross-sectional view similar to FIG. 8, showing the insertion and placement of the occlusal inlay in an abutting relationship with the proximal inlays and covering the prepared cavity;

FIG. 10 is a cross-sectional view similar to FIG. 9, showing the occlusal inlay with a handle removed and shaped;

FIG. 11 is a perspective view of one of a plurality of occlusal inlays in accordance with the present invention having a handle to facilitate placement thereof in the occlusal cavity shown in FIGS. 7 and 8;

FIG. 12 is a top view of a restored tooth showing the relationship of the proximal and occlusal inlays;

FIG. 17 is a perspective view of a combined occlusal and proximal inlay suitable for use in the method of the present invention, as hereinafter described.

DETAILED DESCRIPTION

Figure 1:
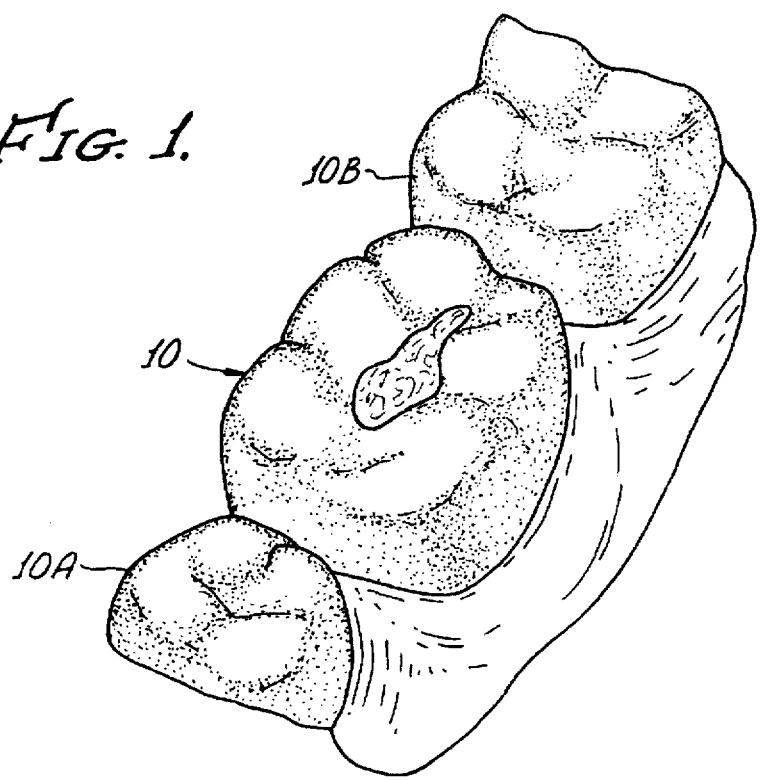
FIG. 1 is a perspective view of a decayed tooth suitable for restoration by the method of the present invention utilizing the dental restoration system.
Figure 2:
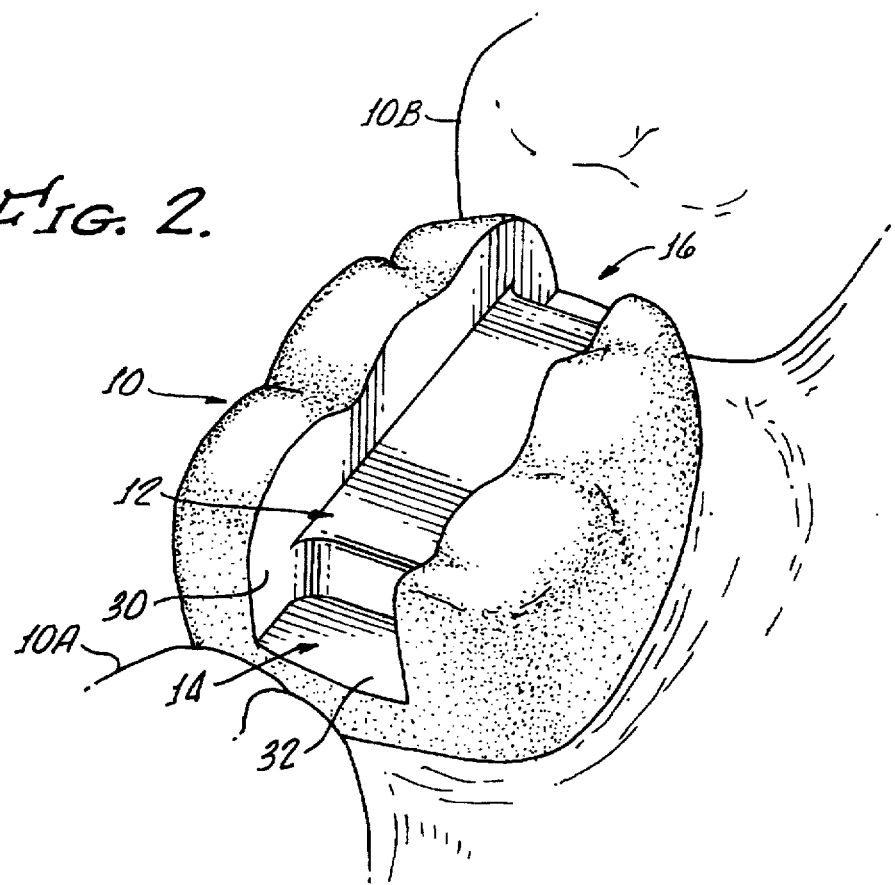
FIG. 2 is a perspective view of a prepared tooth cavity having a mesial-occlusal-distal (MOD) preparation.

Turning now to FIGS. 1 and 2, indicated tooth 10 as shown in FIG. 1 is prepared by forming a prepared cavity 12 in a conventional manner, with the cavity 12 having two ends 14 and 16.

Figure 3:
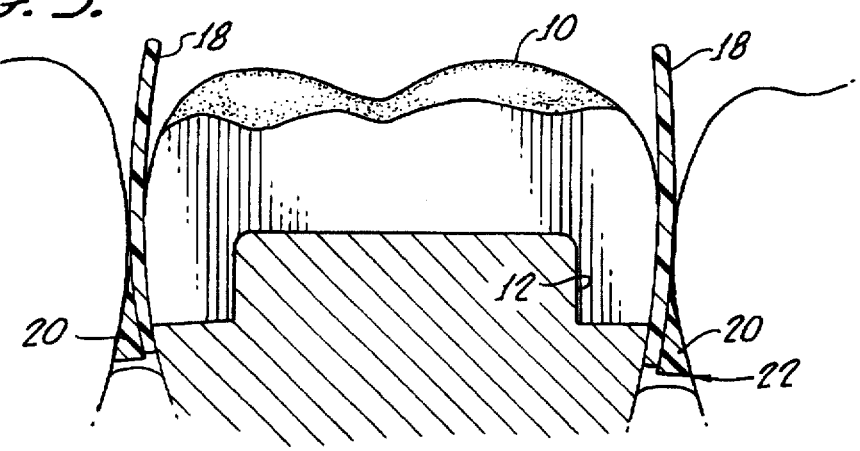
FIG. 3 is a cross-sectional view of the prepared tooth cavity as shown in FIG. 2, showing the insertion of a Tafelmire-type retainer proximate ends of the prepared cavity.
Figure 4:
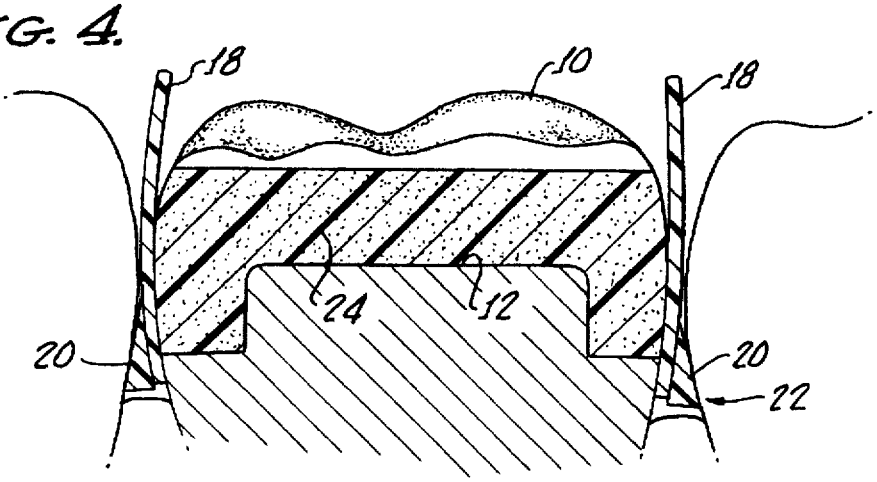
FIG. 4 is a cross-section similar to FIG. 3, showing an uncured restorative resin disposed in the prepared cavity between the retainers.
Figure 5:
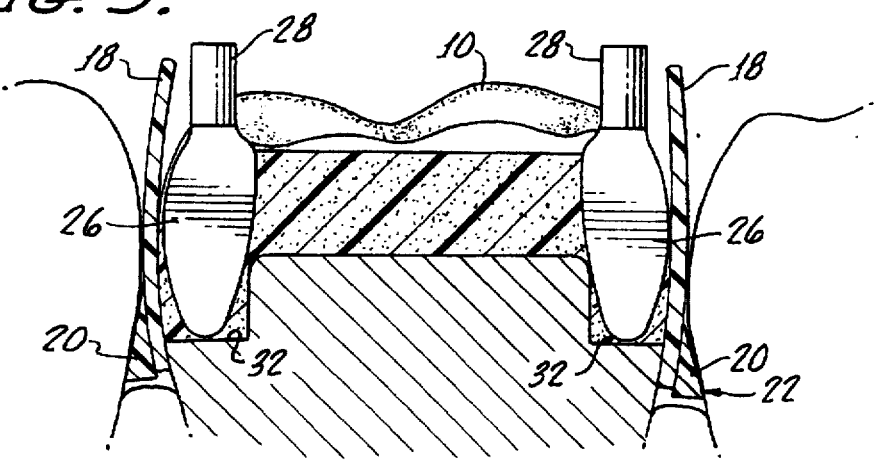
FIG. 5 is a cross-section similar to FIG. 4, showing the insertion of two proximal inlays into the prepared cavity and blocking the ends thereof.

After preparation, the tooth 10 is surrounded with a dental wire-type container 18 and a conventional wedge 20 is disposed at a gingival margin 22, as shown in FIGS. 3-5.

As shown in FIG. 4, the prepared tooth cavity 12 is at least partially filled with an uncured restorative composite resin 24 with insertion of proximal inlays 26 which are disposed for blocking the ends 14, 16 of the prepared tooth cavity 12.

As shown in FIG. 5, insertion of the proximal inlays 26 is facilitated by handles 28 formed therein.

Preferably, the proximal inlays 26 are sized and shaped to frictionally engage at least one wall 30 of the prepared tooth cavity (see FIG. 2). The proximal inlays 26 are seated in the proximal blocks 32 as shown in FIGS. 5-10. Thereafter, the resin 24 is cured in a conventional manner. It should be appreciated that any restorative composite resin material may be utilized in accordance with the present invention, with such materials including, but not limited to, acrylics, urethane and the like, or composite lutting agents, both light-cured and self-cured, with self-cured types being preferred for inlays which fill the cavity to a high degree.

Figure 6:
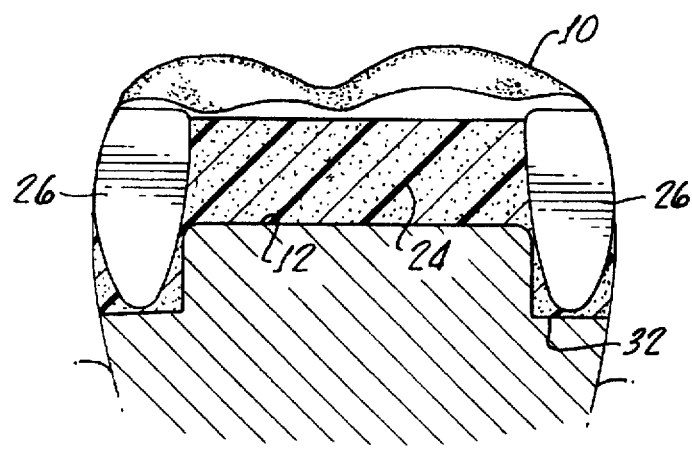
FIG. 6 is a cross-sectional view similar to FIG. 5, showing the proximal inlays with handles removed and secured in a cured restorative resin.

Following the curing of the resin 24, the retainers 18 are removed and handles 28 also removed from the proximal inlays 26, as shown in FIG. 6. Wedges 22 which may be wooden, plastic, or the like are also removed. It should be appreciated also that the thickness of the Tafelmire retainer 18, or other suitable matrix material, is selected for enabling the wedging of adjacent contacting teeth 10a, 10b (see FIGS. 1 and 2) away from the subject tooth 10.

Figure 7:
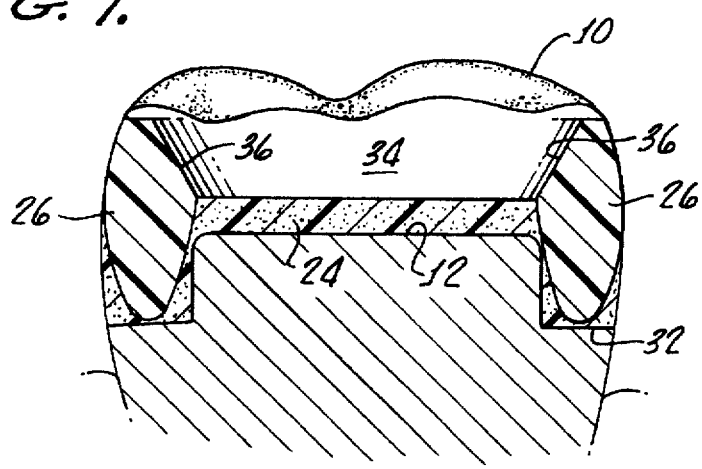
FIG. 7 is a cross-sectional view similar to FIG. 6, showing removal of a majority of the cured resin along with preparation by shaping of the secured proximal inlays for accepting an occlusal inlay.

As shown in FIG. 7, an occlusal cavity is formed by removal cured resin 24 and shaping of proximal inlays 26 to form contact surfaces 36 thereon. The proximal inlays 26 may be oversized in order that the dentist can shape the proximal inlays 26 to achieve the efficient contact of areas 36.

The restoration system and method in accordance with the present invention enables the proximal inserts 26 to be forced against the proximal box 32 and against the prepared cavity walls 30 to ensure competent contact.

Figure 8:
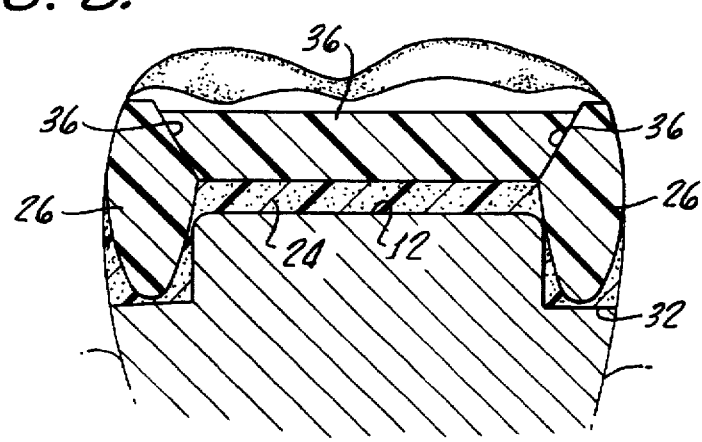
FIG. 8 is a cross-sectional view similar to FIG. 7, showing additional uncured resin being disposed in the occlusal cavity established between proximal inlays.

Turning to FIG. 8, the occlusal cavity 34 is then at least partially filled with additional uncured restorative composite resin 36. Thereafter, as shown in FIG. 9, an occlusal inlay 38 is inserted into the additional uncured restorative resin 36 via the handle 40. Forcing of the occlusal inlay 38 into the additional uncured restorative resin 36 results in a thin bond line 42 of cured resin established between the occlusal inlay 38, cured resin 24 and the proximal inlays 26.

FIG. 11 shows a perspective view of one of the plurality of occlusal inserts 38, with handle 40 thereon for facilitating placement thereof in restorative position with the prepared tooth cavity 12. While any number of shapes may be utilized, the tapered ends 44 of the occlusal inlay 38 facilitate its placement within the occlusal cavity 34 (FIG. 7), as shown in the top view in FIG. 12.

Figure 13:
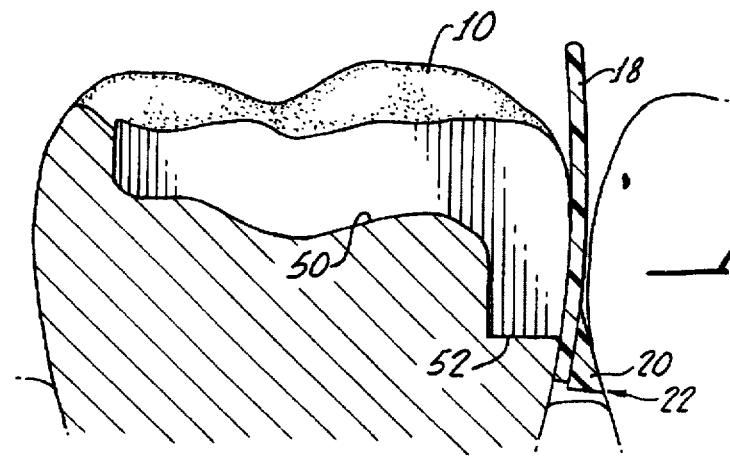
FIG. 13 is similar to FIG. 3 except the prepared tooth cavity has only one end.
Figure 14:
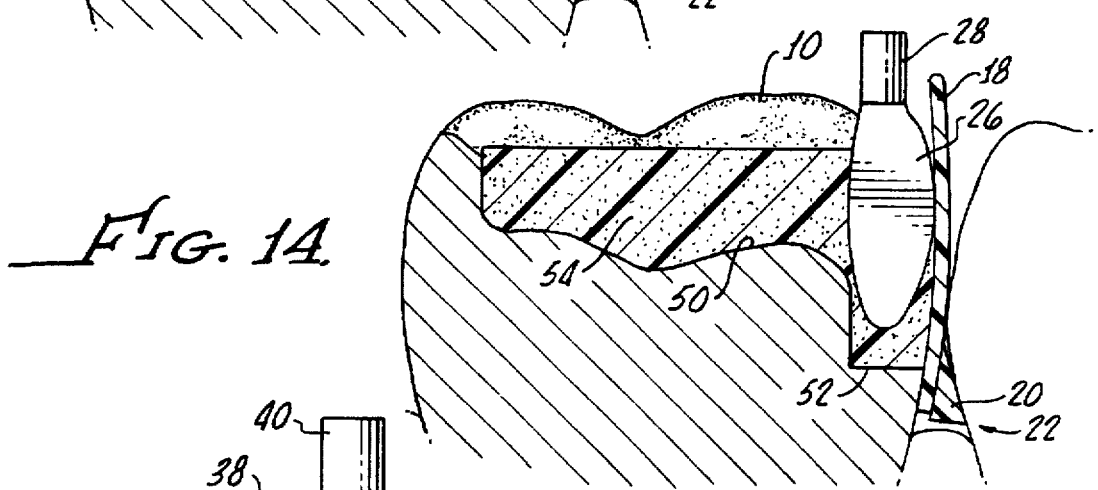
FIG. 14 is similar to FIG. 5 but showing insertion of only one proximal inlay.

FIGS. 13-16 show the use of the proximal inlays 26 in occlusal inlays 38 in a prepared cavity 50 having only one proximal box 52. As hereinabove described, the Tafelmire retainer is inserted along with a wedge 20, as shown in FIG. 13.

Thereafter, the proximal inlay 26 is inserted into the proximal 52 and the resin 54 disposed in the cavity 50.

Thereafter, as also hereinabove described, a cured restorative resin 52 is removed to form an occlusal cavity 56 with a tapered side 58 being formed in the proximal inlay 26 after removal of the handle 28 and a matching surface 60 formed in the cured resin 54. Following insertion of additional uncured resin and the occlusal inlay 38, thereafter the occlusal inlay 38 and proximal inlay 26 are shaped as hereinabove described.

Figure 15:
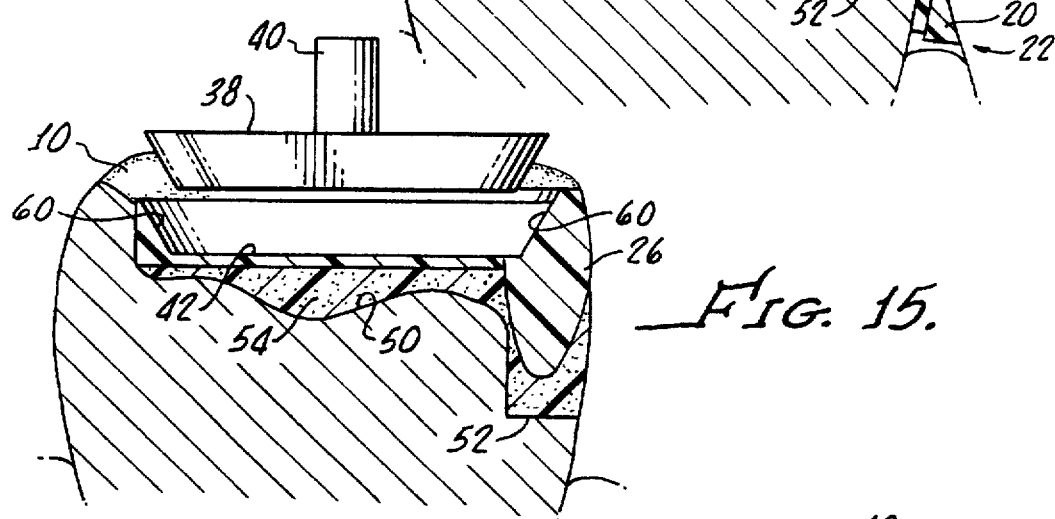
FIG. 15 is similar to FIG. 9 showing an insertion of an occlusal inlay in a prepared occlusal cavity.
Figure 16:
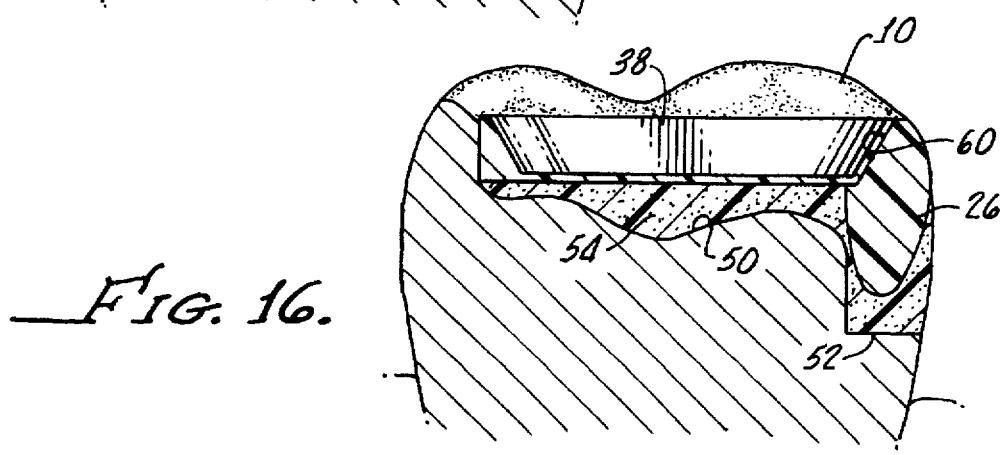
FIG. 16 is similar to FIG. 10 showing completed restoration.

Alternatively, the restoration system in accordance with the present invention may include a combined proximal/occlusal inlay 70 as shown in FIG. 17 suitale for modular-occlusal (MO) restorations. This inlay 70 includes a proximal portion 72 and an occlusal portion 74 joined at generally right angles. The handle 76 facilitates placement of the proximal/occlusal inlay 70 into the prepared cavity 50, as generally shown in FIGS. 15–16. Insertion and shaping of the inlay as formed as hereinabove described in connection with the separate proximal inlays 26 and occlusal inlays 38.

The present invention, as hereinabove described, provides a combination of the majority of the best features, both direct and indirect, of restorations hereinabove available. The procedures as hereinabove set forth are as fast as a direct composite restoration, thus eliminating second office visits. In addition, polymerization shrinkage of the composite is reduced to a minimum and the margins are small and approach those of a typical lutting agent present in a custom inlay, i.e., an inlay made in a dental laboratory from an impression of the actual cavity preparation. The contacts provided by the restoration system in accordance with the present invention are positive and durable and further durability and low wear resistance of the inlays 26, 36 is provided by their composition from dental porcelain, ceramic, or quartz glass ceramic, as is well known.

Although there has been hereinabove described a specific dental restoration system and method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A dental restoration system comprising:
   at lease one proximal inlay including means, defining a size thereof, for blocking an end of a prepared tooth cavity and enabling a tapered contact area to be shaped thereon;
   an occlusal inlay including means, defining a size and shape thereof, for covering said prepared tooth cavity and facilitating placement of the occlusal inlay in a position abutting the proximal inlay tapered contact area, the last mentioned means comprising a tapered end on the occlusal inlay; and
   curable restorative resin means for securing the proximal inlay in a blocking relationship with the end of said prepared tooth cavity and for securing said occlusal inlay to a bottom of said prepared tooth cavity and to the proximal inlay.

2. The dental restorative system according to claim 1 wherein each of the proximal and occlusal inlays comprises removable handle means for facilitating placement thereof in a restorative position with said prepared tooth cavity.

3. The dental restorative system according to claim 2 wherein each of the proximal and occlusal inlays is composed of dental porcelain.

4. The dental restorative system according to claim 2 wherein each of the proximal and occlusal inlays is composed of ceramic.

5. The dental restorative system according to claim 2 wherein each of the proximal and occlusal inlays is composed of quartz glass ceramic.

6. The dental restorative system according to claim 1 wherein the proximal inlay is shaped to frictionally engage at least one wall of said prepared tooth cavity.

7. A dental restorative system comprising:
   a first proximal inlay including means, defining a size thereof, for blocking an end of a prepared tooth cavity and enabling a tapered contact area to be shaped thereon;
   a second proximal inlay including means, defining a size thereof, for blocking another end of said prepared tooth cavity and enabling a tapered contact area to be shaped thereon;
   an occlusal inlay including means, defining a size and shape thereof, for covering said prepared tooth cavity and facilitating placement of the occlusal inlay in a position abutting both the first and second proximal inlays inlay tapered contact areas, the last mentioned means comprising tapered ends on the occlusal inlay; and
   curable restorative resin means for securing the proximal inlays in a blocking relationship with the ends of said prepared tooth cavity and for securing said occlusal inlay to a bottom of said prepared tooth cavity and to both the first and second proximal inlays.

8. A dental restorative system comprising:
   a plurality of proximal inlays, each proximal inlay including means, defining a different size thereof, for blocking an end of a prepared tooth cavity and enabling a tapered contact area to be shaped thereon;
   a plurality of occlusal inlays, each occlusal inlay including means, defining a different size and shape thereof, for covering said prepared tooth cavity and facilitating placement of each occlusal inlay in a position abutting at least one of the plurality of proximal inlay tapered contact areas, the last mentioned means comprising at least one tapered end on each occlusal inlay; and
   curable restorative resin means for securing said at least one of the plurality of proximal inlays in a blocking relationship with the end of said prepared tooth cavity and for securing one of said plurality of occlusal inlays to a bottom of said prepared tooth cavity and to said at least one of the plurality of proximal inlays.

9. The dental restorative system according to claim 8 wherein another of said plurality of proximal inlays and another of said plurality of occlusal inlays are joined at a generally right angle with one another.

10. The dental restorative system according to claim 8 wherein each of the proximal and occlusal inlays comprises removable handle means for facilitating placement thereof in a restorative position with said prepared tooth cavity.

11. The dental restorative system according to claim 8 wherein each of the proximal and occlusal inlays is composed of dental porcelain.

12. The dental restorative system according to claim 8 wherein each of the proximal and occlusal inlays is composed of ceramic.

13. The dental restorative system according to claim 8 wherein each of the proximal and occlusal inlays is composed of quartz glass ceramic.

14. The dental restorative system according to claim 8 wherein each of the proximal inlays is shaped to frictionally engage at least one wall of said prepared tooth cavity.

15. A dental restoration system comprising:

at least one proximal inlay including means, defining a size thereof, for blocking an end of a prepared tooth cavity and enabling a tapered contact area to be shaped thereon;

an occlusal inlay including means, defining a size and shape thereof, for covering said prepared tooth cavity and facilitating placement of the occlusal inlay in a position abutting the proximal inlay, tapered contact area, the last mentioned means comprising a tapered end on the occlusal inlay.

16. A dental restoration system comprising:

a proximal inlay including means, defining a size thereof, for blocking an end of a prepared tooth cavity and enabling a tapered contact area to be shaped thereon;

a combinal proximal/occlusal inlay having a depending proximal means, disposed on one end thereof, for blocking another end of the prepared tooth cavity and body means for covering said prepared tooth cavity and facilitating placement of the combined proximal/occlusal inlay in a the proximal inlay tapered contact area, said body means comprising a tapered end disposed on another end of the combined proximal/occlusal inlay.

\* \* \* \* \*